United States Patent [19]

Casagrande et al.

[11] Patent Number: 4,628,064
[45] Date of Patent: Dec. 9, 1986

[54] EPININE AND THE THERAPEUTIC USE THEREOF

[75] Inventors: Cesare Casagrande, Arese; Paolo Ghirardi, Milan, both of Italy; Leon I. Goldberg, Chicago, Ill.; Germano Marchetti, Milan, Italy

[73] Assignee: SIMES, Societa Italiana Medicinali e Sintetici S.p.A., Milan, Italy

[21] Appl. No.: 631,751

[22] Filed: Jul. 17, 1984

[30] Foreign Application Priority Data

Jul. 19, 1983 [IT]  Italy ............................ 22118 A/83

[51] Int. Cl.⁴ .......................................... A61K 31/135
[52] U.S. Cl. ...................................................... 514/654
[58] Field of Search ............................. 514/654, 653

[56]  References Cited

U.S. PATENT DOCUMENTS 3,966,905  6/1976  Nite ....................................... 424/80
4,181,738  1/1980  Ginos et al. ........................ 424/330
4,218,470  8/1980  Casagrande et al. .............. 424/311
4,219,568  8/1980  Goldberg ............................ 514/654

FOREIGN PATENT DOCUMENTS 2320646  11/1974  Fed. Rep. of Germany .

OTHER PUBLICATIONS

Chem. Abst. 89 772(r) (1978)—Chavdarian et al.
Chem. Abst. 96 155235(m) (1982)—Soustre et al.
The Merck Index 9th (1976)—Item 2866, Merck & Co., Inc.
Chem. Abst. vol. 82, No. 9, p. 52, Item 51670u (1975).
Chem. Abst. vol. 95. No. 16, p. 373, Item 138500f (1981).

*Primary Examiner*—Douglas W. Robinson
*Attorney, Agent, or Firm*—Cushman, Darby & Cushman

[57]  ABSTRACT

Pharmaceutical compositions which contain epinine or a pharmaceutically acceptable salt thereof, and allow to reach a release of epinine comprised between 0.5 and 5 µg/Kg/minute.

Said compositions are useful in treating congestive heart failures; they stimulate the heart contractility, show a vasodilating and bronchodilating activity as well as a vasodilating activity on specific districts and particularly on the renal district without causing vasoconstrictive and pressor effects.

5 Claims, No Drawings

EPININE AND THE THERAPEUTIC USE THEREOF

This invention relates to pharmaceutical compositions for treating congestive heart failures containing epinine or a pharmaceutically acceptable salt thereof.

Epinine(N-methyl-3,4-dihydroxyphenethylamine) is a cathecolamine like substance structurally related to adrenaline, and is known since the beginning of this century (Pyman, J. Chem. Soc., 95, 1266, (1909), 1610).

The early pharmacological studies date back to Barger and Dale (J. Physiol. 41, (1910), 19) who proved the hemostatic and vasoconstrictive and pressor effect of epinine.

Epinine has been systemically studied by C. A. Crismon, M. L. Tainter (J. Pharmacol., 66, (1939), 146 and above cited literature) who considered it as a useful pressor agent, even if less potent than adrenaline (about ten times); a similar profile was provided by A. M. Hjort (A. M. Hjort, J. Pharmacol. Exptl. Therap., 50, (1933), 131; A. M. Hjort, E. J. De Beer, L. O. Randall, J. Pharmacol. 71, (1941), 105).

Subsequent pharmacolgical studies showed that epinine is endowed with other pharmacological effects; however, the alpha-adrenergic activity which is responsible for the pressor effect appeared to be the prevalent one, thus precluding therapeutic uses other than those previously suggested.

In 1968 Goldberg (L. I. Goldberg, P. F. Sonneville, J. L. McNay, J. Pharmacol. Exptl. Therap., 163, (1968), 188), in a comparative study carried out on 44 compounds having phenethylamine structure showed that only epinine was endowed with a dopaminergic activity similar to that of dopamine; however, the stronger alpha-adrenergic vasoconstrictive effect of epinine predominated on the renal vasodilating effect; the Author thus came to the conclusion that by administering epinine it was impossible to reach a therapeutic effect similar to that of dopamine, which had been proposed as a drug useful for the treatment of refractory heart failure (L. I. Goldberg, Am. J. Cardiology, 22 (1968), 177; Pharmacol. Rev. 24, (1972), 1).

It has been surprisingly found that epinine when administered by venous infusion or by oral route in suitable pharmaceutical formulations which allow a suitable release, instant by instant, stimulates the heart contractility (action on $beta_1$-adrenergic receptors) and exhibits a vasodilating activity (action on $beta_2$-adrenergic receptors) as well as a vasodilating activity on specific districts and particularly on the renal district (action on postsynaptic $DA_1$ dopaminergic receptors) without causing any vasoconstrictive or pressor effect.

More particularly, it has now been found that these useful pharmacological actions are obtained when a pharmaceutical composition is used which allows epinine to reach an instant by instant level comprised between 0.5 and 5 $\mu$g/kg/min.

Furthermore, it has been found that epinine, at the above mentioned levels, is more advantageous than dopamine in that (differently from dopamine itself) it reduces the heart rate and its vasodilating effect (by stimulation of the presynaptic dopaminergic receptors) remarkably higher than that of dopamine.

Owing to the above mentioned pharmacological actions, the new pharmaceutical compositions of this invention are useful in treating heart failure, more particularly in severe patients who do not suitably respond to the usual treatment with digitalis and diuretics; such a therapeutic effect is the combination of the direct inotropic effect on the $beta_1$-receptors, of the lack of increase for the heart rate, of the systemic vasodilating effects on the vascular $beta_2$-receptors and on the presynaptic $DA_2$-receptors, of the bronchodilating effect on the $beta_2$-receptors, of the renal vasodilating and diuretic effects mediated by the $DA_1$ receptors.

The higher vasodilation of the general and of the pulmonary circulatory system which is correlated to the $beta_2$ and to the presynaptic $DA_2$ effect is particularly useful in that it causes a better perfusion of striated muscles and of the mesenteric district. The better perfusion of the striated muscles together with an increase oxygen supply is advantageous in that allows the patient to exert a more intense and prolonged physical activity without dyspnea symptoms. Furthermore, the marked increase of cardiac output effect without any increase of and even a slight redution of the heart rate is another favorable feature because it reduces the risk of anginal and arrhythmic effects which are often present in patients suffering from heart diseases.

The greater bronchodilating effect is also useful to prevent bronchospasm and athsma which are sometimes present in patients suffering from heart failure.

These useful pharmacological activities are obtained when epinine is administered at a level comprised between 0.5 and 5 $\mu$g/kg/min.

Dopamine and epinine have been compared after intravenous infusion at different doses in the anesthetized dog. The results obtained by these tests are summarized in tables 1 and 2.

Dopamine and epinine, at doses of 1, 2.5 and 5 $\mu$g/kg/min gave similar responses as far as the arterial pressure, renal flow and renal resistances are concerned; on the contrary the effect on the heart rate was different in that it was slightly increased by dopamine whereas epinine caused a moderate but significant reduction of the heart rate.

In the preparation of the electrically stimulated median arteria of rabbit ear (according to the method described by Nelson and Steinsland, J. Pharm. Exptl. Therap. 244 (1983), 193) epinine and dopamine tested at different concentrations comprised between 0.01 and 10 $\mu$M have shown a clearly different behaviour in inhibiting the contraction induced by electrical stimulation; $ED_{50}$ were 0.077 $\mu$M and 2.39 $\mu$M for epinine and, respectively, for dopamine.

Neither compound prevented the vasoconstriction caused by intraluminal infusion of norepinephrine; it can therefore be concluded that the activity of the above mentioned compounds is exerted on the presynaptic $DA_2$ receptors by inhibiting the release of the neurotransmitter. The activity of epinine was 30 times higher than that of dopamine.

The pharmaceutical compositions which are an object of this invention may contain epinine as such or, preferably, as a salt with a non toxic organic or inorganic acid suitable for pharmaceutical use; hydrochloride is a preferred embodiment of this invention owing to the solubility and stability of this salt.

The compositions are prepared to allow a suitable therapy by intravenous route with doses comprised between 0.5 and 5 $\mu$g/kg/min and an oral therapy with doses of epinine hydrochloride comprised between 400 and 1600 mg/day which secure the release of about 0.5 and 5 $\mu$g/kg/min for about 6 hrs.

TABLE 1

Modifications of hemodynamic parameters in the anesthetized dog after infusion of different doses of epinine
(the values were measured 5 minutes after the infusion of each dose).

| Doses µg/kg/min | Esp. No. | Heart rate | Average arterial pressure (mmHg) | Renal art. flow (ml/min) | Renal resistances (mmHg/ml/min) |
|---|---|---|---|---|---|
| basal | 7 | 163 ± 10 | 140 ± 9 | 150.8 ± 26.8 | 1.031 ± 0.189 |
| 0.50 | 7 | 164 ± 10 | 136 ± 9 | 153.5 ± 18.5 | 0.990 ± 0.145 |
| 1.00 | 7 | 161 ± 11 | 136 ± 8* | 157.5 ± 28.1 | 0.971 ± 0.185** |
| 2.50 | 7 | 156 ± 12 | 135 ± 7 | 159.8 ± 29.3* | 0.954 ± 0.183** |
| 5.00 | 7 | 149 ± 11** | 139 ± 6 | 164.3 ± 29.7* | 0.965 ± 0.181 |

Average values ± SE
*$p < 0.05$
**$p < 0.01$

TABLE 2

Modification of hemodynamic parameters in the anesthetized dog after infusion of different doses of dopamine.
(The values were measured 5 minutes after the infusion of each dose).

| Doses µg/kg/min | Exp. No. | Heart rate | Average arterial pressure (mmHg) | Renal art. flow (ml/min) | Renal Resistances (mmHg/ml/min) |
|---|---|---|---|---|---|
| Basal | 7 | 146 ± 8 | 108 ± 5 | 117 ± 19.6 | 1.212 ± 0.280 |
| 1.00 | 7 | 144 ± 10 | 106 ± 7 | 127 ± 20.8* | 1.120 ± 0.149** |
| 2.50 | 7 | 146 ± 8 | 105 ± 6 | 132 ± 21.0** | 1.053 ± 0.146** |
| 5.00 | 7 | 151 ± 8 | 109 ± 6 | 122.9 ± 19.8** | 1.136 ± 0.261* |

Average values ± S.E.
*$p < 0.05$
**$p < 0.01$

The following examples are given in order to illustrate the invention without limiting its scope.

EXAMPLE 1

Sustained release (about 6 hrs) tablets.

| | |
|---|---|
| Epinine hydrochloride | 400 mg |
| Polyvinylpyrrolidone (PVP) | 12 mg |
| Microgranuated cellulose | 100 mg |
| Copolymers of esters of acrylic and metacrylic acids | 20 mg |
| Hydrogenated castor-oil | 8 mg |
| Titanium dioxide | 4 mg |
| Polyethyleneglycol | 1 mg |

PVP is dissolved in 50% ethyl alcohol; after addition of epinine hydrochloride the mixture is then kneaded and granulated; the thus obtained granulate is dried; separately, 50% of the above mentioned amount of acrylic resin is dissoved in a mixture consisting of isopropanol and acetone, kneaded and granulated together with the microgranulated cellulose; the thus obtained granulate is dried. Thereafter, the two granulates are mixed, hydrogenated castor oil is added and the powder is then pressed to afford tablets.

The tablets are film-coated as follows: the remaining 50% of the acrylic resin and polyethyleneglycol are dissolved in a 1:1 mixture of methylene chloride and alcohol; titanium dioxide is uniformly suspended in the thus obtained solution and the tablets are sprayed by this mixture in a rotating basin until a weight increase of from 2.5 to 3% is obtained.

From 1 to 4 of the thus obtained tablets are administered in 24 hrs depending on the conditions of the patients and the desired effects. Preferably, to a patient are administered 3 tablets a day, 1 every 8 hours.

EXAMPLE 2

250 mg vials for dilution in physiologic saline or glucose solution (250–500 ml) to allow the administration by slow intravenous infusion at doses comprised between 0.5 and 5 µg/kg/min depending on the conditions of the patients and of desired effects.

| Composition | |
|---|---|
| Epinine hydrochloride | 250 mg |
| Potassium metabisulphite | 40 mg |
| Water for injectable preparations q.s. to | 5 ml |

Epinine hydrochloride is dissolved in a suitable amount of de-aerated water for injectable preparations (for instance 2.5 kg in 40 liters for the preparation of 10,000 vials); potassium metabisulphite is added; the solution is diluted to the required volume, filtered through a microporous membrane and filled, under nitrogen into 5 ml vials; the vials are then sterilized under suitable conditions, for instance at 120° C. for 20 minutes.

We claim:

1. A method for stimulated heart contractility, vasodilation of the circulatory system and bronchodilation, for treating congestive heart failure in man comprising administering epinine or a pharmaceutical salt thereof at a dose corresponding to from 0.5 to 5 µg/kg/min. of epinine.

2. A method according to claim 1 comprising administering the epinine by venous infusion.

3. A method according to claim 1 comprising administering the epinine orally.

4. A method according to claim 1 comprising injecting the epinine.

5. A method according to claim 4 wherein the injection is intravenously.

* * * * *